United States Patent [19]

Holtkamp, Sr.

[11] Patent Number: Plant 6,917

[45] Date of Patent: Jul. 11, 1989

[54] AFRICAN VIOLET PLANT NAMED VIRGO

[76] Inventor: Reinhold Holtkamp, Sr., Werther Strasse 112, D4294 Isselburg, Fed. Rep. of Germany

[21] Appl. No.: 192,673

[22] Filed: May 10, 1988

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A new and distinct cultivar of African violet named Virgo characterized by its single, very light pink flowers with wavy edges and darker pink center; strong, upright flower stems that curve toward the center to form a compact bouquet above the leaves; medium green, strongly serrated girl-type leaves; profuse flowering, vigorous growth habit, flowering 10–11 weeks after potting, and its long-lasting and non-dropping flowers.

1 Drawing Sheet

The present invention comprises a new and distinct cultivar of African violet plant, botanically known as *Saintpaulia ionantha,* and hereinafter referred to by the cultivar name Virgo.

The new cultivar was referred to during the breeding and selection process by the designation G 24/1, and is a product of a planned breeding program. The new cultivar was originated from a cross made by me in the controlled breeding program in Isselburg, Federal Republic of Germany. The female, or seed parent was a cultivar designated 67. The male, or pollen parent was a cultivar designated 47.

Virgo was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Virgo has not been observed under all possible environmental conditions. The phenotype may vary significantly with variations in environment such as temperature, light intensity and day length. The following observations, measurements and values describe the new cultivar as grown in Haffen, West Germany and Nashville, Tenn. under greenhouse conditions which closely approximate those generally used in commercial practice.

The following traits have been repeatedly observed and are determined to be basic characteristics of Virgo, which in combination distinguish this African violet as a new and distinct cultivar:

(1) Strong, upright flower stems curving slightly toward the center.
(2) Very light pink, single flowers with wavy edges.
(3) Profuse flowering.
(4) Each plant carries 7–8 and more upright flower stems each of which carries 7–9 flowers.
(5) Long lasting, non-dropping flowers.
(6) Vigorous grower.
(7) Plant saleable 10 to 11 weeks after potting.
(8) Seed capsules push slightly through.
(9) Medium green girl-type leaf, wavy, strongly serrated with a bright light green center.

(10) After maturity the flowers dry off, and remain on the peduncle without becoming infected by botrytis.

The accompanying color photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 2 p.m. in Nashville, Tenn.

Botanical classification: *Saintpaulia ionantha,* Ramat, c.v. Virgo.

Parentage:

*Male parent.*—47.

*Female parent.*—67.

Propagation: The new cultivar holds its distinguishing characteristics through successive propagations by leaf cuttings.

Plant: From 9 cm to 11 cm tall when grown in pots, and approximately 18–21 cm in diameter when fully grown.

*Leaves.*—General form: Oval, girl-type. Diameter: 60–75 mm. Texture: Velvety. Aspect: Shiny, wavy, very serrated, slightly hairy, bright light green center. Veins: Upperside: well visible, light green radiating from the center; Underside: very well pronounced, light green, shiny, on young leaves slightly purplish. Color (upperside): Yellow-Green Group 147 A. Color (underside): Greyed-Green Group 193 A. Petiole: Strong upright, light green with purplish touch, hairy.

*Flowers.*—Buds: Ball-shaped, 8–9 mm just before opening, light pink. Sepals: Five (5). Color: Purplish brown. Calyx: Shape: Funnel-shaped. Aspect: Spear-shaped, hairy. Peduncle: Character: Strong upright, hairy. Color: Purplish brown. Individual flowers: Size: 35–40 mm. Shape: Single violet-shaped (3 large and 2 small petals), with wavy edges. Color (upperside): Red-Purple Group 62 between C and D. The color may vary with seasonal changes. Under cooler temperatures and more intensive lighting, the pink tends to intensify. Color (underside): Red Group 56 B. Borne: Each flower stem carries 7–9 flowers on strong upright peduncle that are free standing above the leaves, thereby forming a compact bouquet. Flowering habit: Flowers 10–11 weeks after potting.

*Reproductive organs.*—Stamens: Two (2). Anthers: 2 composed of 4 anther cells, seed capsule pushes slightly through. Filaments: Yellowish green with pink traces, 4 mm long. Pollen Color: Yellow Group 7. Styles: 7 mm long, pink, base of ovary light green and hairy.

*Roots.*—Normally developed, white when young, turning slightly brownish when older.

Disease resistance: Good.

General observations: Virgo has a very attractive appearance due to its medium green, strongly serrated girl-type leaves with a light green center. A tight bouquet of flowers free standing above the leaves develops after approximately 10–11 weeks. Each of the 7–8 and more flowers stems carries 7–9 very light pink, single, violet-shaped flowers with wavy edges. The pink color in the center of the flower is darker and radiates somewhat into the two smaller petals. Occasionally, 1–2 additional small petals may develop. The flowers are long-lasting and non-dropping.

I claim:

1. A new and distinct cultivar of African violet named Virgo, as described and illustrated, and particularly characterized by its single, very light pink flowers with wavy edges and darker pink center; strong, upright flower stems that curve toward the center to form a compact bouquet above the leaves; medium green, strongly serrated girl-type leaves; profuse flowering, vigorous growth habit, flowering 10–11 weeks after potting, and its long lasting and non-dropping flowers.

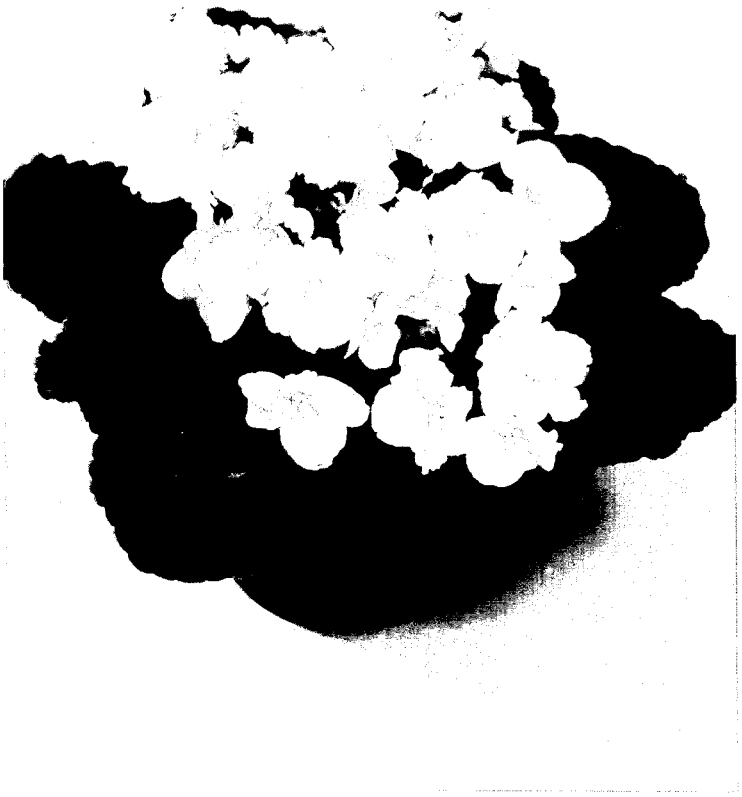

* * * * *